US005711934A

United States Patent [19]
Adjei et al.

[11] Patent Number: 5,711,934
[45] Date of Patent: Jan. 27, 1998

[54] PROCESS FOR THE CONTINUOUS MILLING OF AEROSOL PHARMACEUTICAL FORMULATIONS IN AEROSOL PROPELLANTS

[75] Inventors: Akwete L. Adjei, Wadsworth; Dennis Y. Lee, Highland Park; Anthony J. Hlinak, Lindenhurst, all of Ill.

[73] Assignee: Abbott Laboratories, Abbott Park, Ill.

[21] Appl. No.: 226,132

[22] Filed: Apr. 11, 1994

[51] Int. Cl.$^6$ ........................................... A61K 9/12
[52] U.S. Cl. ........................................... 424/45; 424/46
[58] Field of Search ............... 424/45, 46; 128/200.14, 128/200.21, 200.23; 396/470

[56] References Cited

U.S. PATENT DOCUMENTS

| | | | |
|---|---|---|---|
| 5,118,494 | 6/1992 | Schultz et al. | 424/45 |
| 5,202,110 | 4/1993 | Dalby et al. | 424/45 |

FOREIGN PATENT DOCUMENTS 08447  5/1992  WIPO.

Primary Examiner—Raj Bawa
Attorney, Agent, or Firm—Mona Anand

[57] ABSTRACT

The present invention provides a process for the continuous milling of aerosol pharmaceutical formulations which contain solids by milling in the aerosol propellant.

6 Claims, 1 Drawing Sheet

PROCESS FOR THE CONTINUOUS MILLING OF AEROSOL PHARMACEUTICAL FORMULATIONS IN AEROSOL PROPELLANTS

FIELD OF THE INVENTION

The present invention relates to manufacturing processes and apparatus for preparing pharmaceutical formulations. More particularly, the present invention concerns apparatus and process for preparing aerosol pharmaceutical formulations by milling the formulation in the aerosol propellant.

BACKGROUND OF THE INVENTION

It is desirable to deliver certain therapeutic agents to patients in the form of an aerosol spray. This mode of administration is particularly adapted to situations where the desired site of medication is the upper respiratory tract and also in those situations where systemic administration is desired, but the therapeutic agent cannot be delivered orally. Peptide therapeutic agents, for example, are generally degraded by enzymes present in the mouth and alimentary tract and must be delivered by either a parenteral route or directly to the lungs of the patient by means of an aerosol spray. The latter route of administration is preferred by patients as more convenient and comfortable and less invasive.

Aerosol pharmaceutical formulations can take the form of either a liquid or a solid therapeutic agent suspended or dissolved in a suitable carrier and propellant. The preparation of aerosols in which the active component is a liquid is rather straightforward. However, in the case of solid therapeutic agents, the preparation of aerosol dosage forms is somewhat more complicated.

Typical processes for the preparation of aerosol pharmaceutical formulations which contain solid therapeutic agents involves a multiple-step process in which the solid components of the aerosol dosage form are first milled in air or in a liquid milling medium to obtain the desired particle size. In a second step, where the solids were milled in a liquid medium, the milling medium is removed by filtration or evaporation to leave a cake of the solids. In either case, the cake of solids resulting from the milling step is next broken up and passed through sieves of appropriate size to screen out any aggregates which may be present. The resulting powder, of the desirable particle size range, is then mixed with the aerosol propellant and any desired liquid carrier or additives and filled into the aerosol canisters destined for use by the patient.

The air milling process suffers from the disadvantages of possible contamination of the solids by moisture (with attendant caking and aggregation) and the need for containment facilities to prevent dust explosion and worker exposure. The liquid milling process suffers from similar disadvantages. The use of a liquid milling medium, while aiding in the efficient reduction of the particle size of the solids, requires the additional steps of its removal and subsequent treatment of the resulting solids cake. Moreover, the step of sieving the milled solids often requires special equipment or containment precautions to likewise prevent contamination of the dry solid by moisture, dust explosion hazards, or worker exposure to the therapeutic agent. While in most cases the solid aggregates which are screened out in the sieving step can be recycled in the process, there are some resultant losses which may introduce unacceptable processing costs in those cases where the therapeutic agent is expensive. Further, the liquid milling medium, which cannot be completely removed from the final product during processing of the aerosol formulation, is itself a source of contamination of the final product.

Finally, both air and liquid milling causes the generation of heat which may cause degradation of the therapeutic agent in certain cases.

SUMMARY OF THE INVENTION

Figure 1:
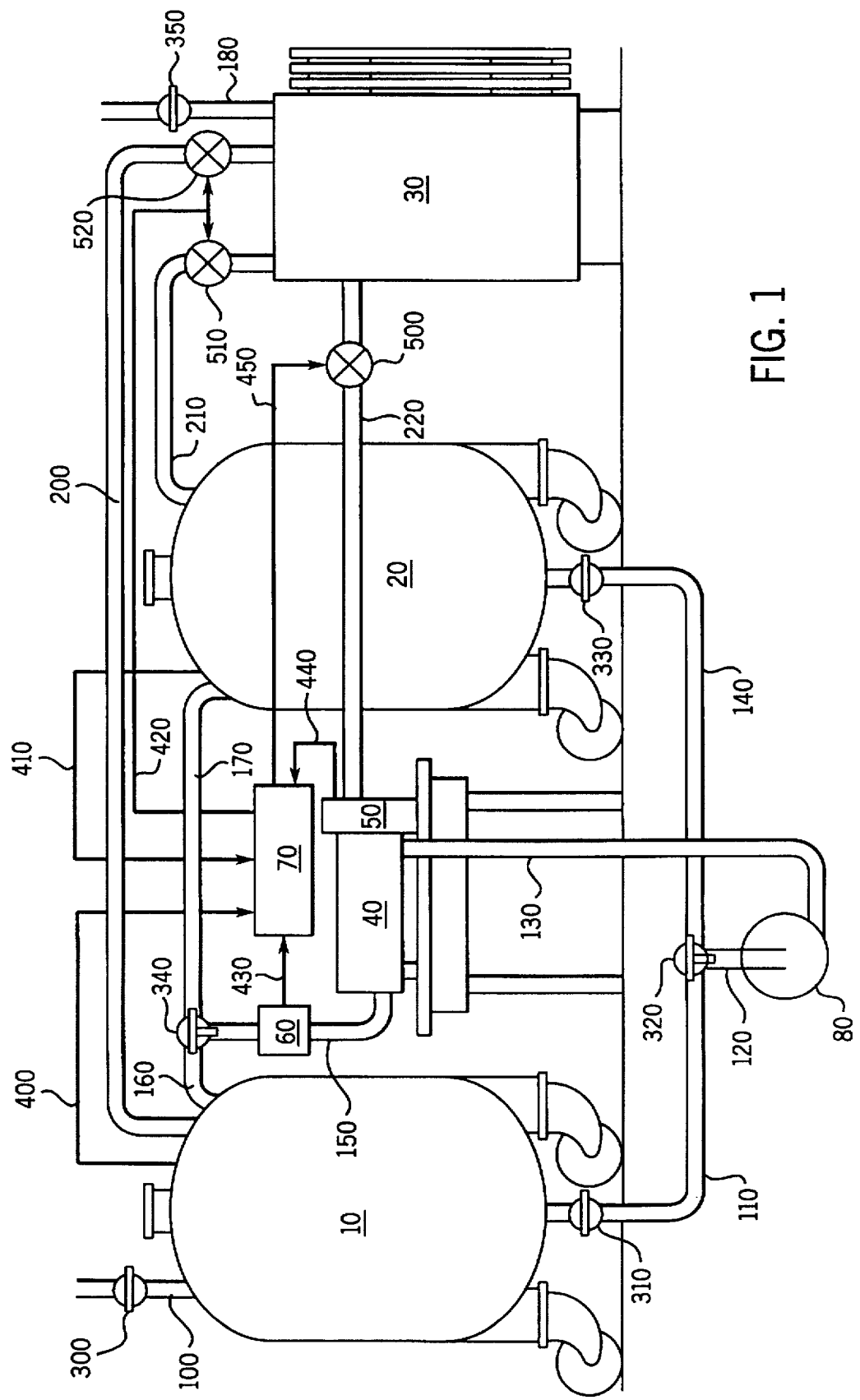
FIG. 1 is a schematic representation of the process and apparatus of the present invention.

The present invention overcomes these disadvantages by providing an apparatus and process for preparing aerosol pharmaceutical formulations containing solid components. In its process embodiment, the invention comprises the step of milling the solid components of the formulation directly in the material which serves as the propellant in the final aerosol formulation. The process thus retains the advantages of milling in a liquid medium but eliminates the need for the use of a distinct liquid milling medium which must be removed before mixing the solids components of the aerosol formulation with the propellant.

In its apparatus embodiment, the present invention comprises an apparatus for continuous milling of aerosol pharmaceutical formulations in an aerosol propellant comprising a) a first supply tank having cooling means for holding a supply of aerosol pharmaceutical formulation; b) a second receiving tank having cooling means; c) a milling apparatus interconnected between said supply and receiving tanks for reducing the solid particle size of said aerosol pharmaceutical formulation; d) pump means for passing said aerosol pharmaceutical formulation from said first supply tank through said milling machine to said second receiving tank; and e) refrigeration means for circulating a coolant through the cooling means of said first supply and said second receiving tank.

DETAILED DESCRIPTION

Throughout this specification and the appended claims, the term "propellant/milling medium" is used to denote the material which is employed in the milling process for liquid milling of the solid therapeutic agent and any additional solid ingredients of the aerosol formulations and which remains in the aerosol formulation to ultimately function in the role of propellant.

The propellant/milling medium is selected from materials in which the desired therapeutic agent is insoluble in order to produce a final aerosol formulation in which the therapeutic agent is suspended in finely divided particulate form. In certain situations, two or more therapeutic agents may be incorporated into the final aerosol formulation. In these cases, the different therapeutic agents may be milled together in the propellant/milling medium or, alternatively, the therapeutic agents can be milled separately in the same or different propellant/milling media to the desired particle size or sizes and the resulting suspensions mixed prior to filling the aerosol canisters. The latter alternative is useful in those cases where the nature of the two or more therapeutic agents is such that the desired particle size ranges for the agents are different.

Likewise, it is possible to use two or more materials in admixture as the propellant/milling medium. Alternatively, the therapeutic agent or mixture of agents can be milled in a single propellant/milling medium, and one or more propellant materials added at later stages of the process. It should be noted however, that in all of the variants of the process described above, the process of the present invention does not involve removing any material added during the process steps. That is, each ingredient added to the aerosol formulations during processing becomes a part of the final formulation and is present in the final formulation. In this manner the process of the present invention differs from prior art processes for preparing solid aerosol formulations where milling media added during the milling steps must be removed prior to final formulation of the aerosol.

Suitable materials for use as the propellant/milling medium in the process of the present invention are those materials which possess a high vapor pressure at room temperature, are chemically compatible with the therapeutic agent or agents contained in the aerosol formulation, and in which the therapeutic agent or agents are not soluble. Representative propellant/milling media for use in the process of this invention include low-boiling lower alkanes, low-boiling halogenated lower alkanes, low-boiling lower cycloalkanes, low-boiling halogenated lower cycloalkanes, low-boiling di-(lower alkyl)ethers, low-boiling halogenated di-(lower alkyl)ethers, low-boiling di-(lower alkyl) thioethers, and low-boiling halogenated di-(lower alkyl) thioethers and the like. These materials include, by way of example, chlorodifluoromethane, chlorotrifluoromethane, dichlorodifluoromethane, trichlorofluoromethane, tetrafluoroethane, 1,2-dichlorotetrafluoroethane, trichlorofluoroethane, chloropentafluoropropane, chloroheptafluoropropane, heptafluoropropane, perfluorocyclopropane, perfluoropropane, perfluoro-n-butane, perfluoroisobutane, perfluorocyclobutane, perfluorodimethyl ether, perfluorodiethyl ether, perfluorofuran, perfluoromethylamine, bis-(trifluoromethyl)sulfone, bis-(trifluoromethyl)sulfide, and trifluoromethylpentafluorosulfide and the like.

By the term "lower alkane" and "lower cycloalkane" is meant straight or branched or cyclic saturated hydrocarbons of one to ten carbon atoms. The term "low-boiling" means boiling points below human body temperature. Preferred propellant/milling media are those materials having boiling points below about 25° C.

While chlorofluorocarbon materials can be advantageously used in the process of this invention, the current trend in the industry is away from the use of such materials which contain chlorine because of the adverse environmental effects. Preferred propellant/milling media in the process of the present invention thus include the partially or completely fluorinated (i.e. "perfluro") hydrocarbons. Particularly preferred propellant/milling media are tetrafluoroethane and heptafluoropropane.

The process of the present invention can be used to prepare solid aerosol formulations for any solid therapeutic agent for which aerosol administration is a as desirable route of administration. Examples include peptides, protein materials, and other agents which do not lend themselves to oral administration such as interferons and other macrophage activation factors; erythropoietin and other glycoproteins; opioid peptides, neuropeptides, enkephalins, endorphins, dynorphins, peptide and pseudopeptide renin inhibitor agents; cholecystokinins such as cerulitide and eledoisin; leukotrienes and prostaglandins; peptidomimetics; insulin; oxytocin; antiasthmatic agents; and pharmaceutically acceptable salts, esters and pro-drugs of any of the foregoing.

Specific examples of therapeutic agents falling within the aforementioned general classes include, but are not limited to LHRH agonist and antagonists such as leuprolide and its salts (particularly the acetate), antiallergic and antiasthmatic agents such as N-hydroxy-N-(1-(benzo[b]thien-2-yl)ethyl) urea (also known by its generic name "zileuton") antiinflammatory agents such as beclomethasone; albuterol; isoproterenol; ipratropium; flunisolide; terbutaline; pirbuterol; triamcinolone; and the pharmaceutically acceptable salts, esters, or pro-drugs of any of the foregoing.

In aerosol formulations made by the process of this invention, the propellant/milling medium material can comprise up to 99.9% of the mixture. Additional components of the aerosol formulations made by the process of this invention include surfactants which are compatible with the therapeutic agent or agents incorporated into the formulations and in which the therapeutic agent or agents is not soluble. Suitable surfactants include, but are not limited to sorbitan monooleate, sorbitan trioloeate, sorbitan monolaurate, polyoxyethylene (20) sorbitan monooleate, polyoxyethylene (20) sorbitan monolaurate, sodium lauryl sulfate, cholesterol, natural and synthetic lecithins, oleyl polyoxyethylene, stearyl polyoxyethylene, lauryl polyoxyethylene, block copolymers of oxyethylene and oxypropylene, oleic acid, diethylene glycol dioleate, tetrahydrofuryl oleate, ethyl oleate, isopropyl myristate, glyceryl trioleate, glyceryl monolaurate, glyceryl monostearate, cetyl alcohol, polyethylene glycol 440, cetyl pyridinium chloride, and natural oils such as those derived from corn, olives, cotton seed and sunflower seed. In the formulations, the surfactant component comprises generally up to about 3% of the formulation.

Because the propellant/milling medium has a boiling point near or below room temperature, it must be kept refrigerated during the process of milling, typically at temperatures ranging between about −80° C. to about 10° C. This refrigeration also has the advantage of cooling the mixture being milled which prevents any thermal degradation of sensitive therapeutic agents. This is accomplished in the preferred embodiment of the process of the present invention by consecutive passes of the mixture of propellant/milling medium through the milling machine between two tanks alternately serving, respectively, as the supply and receiving tanks, both of which are double-walled with provision for circulating a coolant either through a cooling jacket between the walls of the tank or through cooling coils disposed within the tanks.

The mixture is passed back and forth through the mill until the desired particle size is obtained for the solids content of the mixture. The particle size can be monitored by periodically withdrawing an aliquot sample from the system for particle size analysis by conventional methods or, more conveniently, by continuous in-stream particle size analysis by optical means such as a laser light scattering particle size analyzer incorporated into the process stream. In-stream particle size analysis can be conveniently carried out by the use of, for example, a Partec® 100 model laser light back diffusion particle size analyzer available from Lasentec, Duluth, Ga.

Milling is carried out by use of, for example, a bead mill of the type conventionally utilized in the pharmaceutical formulation arts such as a "Dyno-Mill Type KDL" or "Dyno-Mill Type KDL Special" unit manufactured by W. A. Bachofen AG, Basel, Switzerland. The milling machine may be fitted with a cooling jacket which surrounds the mechanical seal of the rotating shaft of the mill to counteract the production of heat generated during the milling operation. In a particularly unique feature of the process of the present invention, the coolant is circulated through both the tank cooling jackets and the milling machine mechanical seal jacket and is chosen to be identically the same material as that employed as the propellant/milling medium in the milling process. This insures that any leakage of coolant into the milled formulation which might occur at the mechanical seal of the mill does not result in contamination of the batch being milled.

A schematic representation of the apparatus employed in the preferred embodiment of the process appears in FIG. 1. In FIG. 1, process feed lines and coolant feed lines are shown as double lines, while electrical or electronic signal lines are shown as fine lines with an arrowhead at one end indicating the direction of signal flow.

In the preferred embodiment, the process of the invention is carried out using an apparatus which is constructed in modules which are interconnected by quick-connect and quick-disconnect fittings of the type well known in the pharmaceutical processing art. Tanks 10 and 20 are mounted on wheels to permit their movement into position for the milling process and later moved to a location where they serve as supply vessels for the subsequent aerosol canister filling operation. The tanks are double-walled to permit circulation of a refrigerant or coolant through a cooling jacket between the inner and outer walls to cool the contents of the tank as needed and are also constructed to contain pressures above atmospheric. In an alternative embodiment, the double-walled construction of the tanks serves an insulating function and the tank contents are cooled by circulating coolant through coils situated inside the tanks.

The bead mill 40, jacketed mechanical seal 50 and the associated piping, valves, and electronic sensor array are conveniently mounted on a single pad so that they can be moved into place during the milling process or removed for cleaning or any necessary repairs.

An electronically programmable control apparatus 70 receives and processes electrical signals from various sensors located throughout the system to control the flow of refrigerant, to open and close valves as required, and to process other signals such as those from the in-stream particle size analyzer.

A heat exchanger 30 receives cooling water or other commercial refrigerant such as a Freon® through valve 350 and line 180 to cool the refrigerant or coolant which is circulated through coolant feed line 200 to the cooling jacket of tank 10, through coolant feed line 210 to the cooling jacket of tank 20, and through coolant feed line 220 to the cooling jacket of the mechanical seal 50 of bead mill 40. In a control feed-back loop, temperature sensors immersed in the contents of tank 10 send an electrical signal through signal line 400 to controller 70 which, in turn, sends a control signal to electrically operated valve 520 which controls the flow of refrigerant through coolant feed line 200 to control the temperature of the tank contents. In a similar fashion, temperature sensors in tank 20 operate in conjunction with controller 70 through signal lines 410, and 420 and electrically operated valve 510 to supply coolant through line 210 to control the temperature of the contents of the tank.

Mechanical heat which is generated in the mechanical seal 50 of bead mill 40 during the milling process and which would otherwise cause an unacceptable rise in the vapor pressure of the propellant/milling medium, is similarly controlled by the circulation of coolant through coolant feed line 220 to a cooling jacket which surrounds the mechanical seal 50. A temperature sensor in the mechanical seal 50 communicates with controller 70 through signal line 440 and the controller, in turn, signals electrically-controlled valve 500 through signal line 450 to control the flow of coolant to the mechanical seal 50.

A unique feature of the process of the present invention lies in the fact that the coolant which is employed in cooling the contents of tanks 10 and 20 and mechanical seal 50 is the same as the liquid employed as the propellant/milling medium. In this way, any introduction of coolant from the cooling jacket of the mechanical seal 50 into the contents of the bead mill 40 during milling as a result of pressure differences does not result in the contamination of the material in the system.

In the milling of a typical batch of aerosol formulation employing the process and apparatus of the present invention, the propellant/milling medium is charged through feed line 100 and valve 300 to tank 10. The solid to be milled is then mixed, together with other components of the formulation such as surfactants, with the propellant/milling medium under nitrogen gas or other appropriate dry inert gas. Mixing of the materials in either tank 10 or 20 is most conveniently carried out by means of magnetic stirrers located in the tanks. This eliminates problems of contamination or pressure leaks which might otherwise occur with the use of mechanical stirrers whose shafts must pass through the wall of the tanks.

The mixture of solids and propellant/milling medium contained in tank 10 is next transferred through valve 310 and feed line 110 and three-way valve 320 to pump 80 which forces the mixture through feed line 130 to the bead mill, 40. The material exits the bead mill 40 through feed line 150 where it passes through an in-line particle size analyzer 60. From there the material passes through three-way valve 340 and feed line 170 to tank 20 which serves as the receiving tank for the first pass of the material through the milling process. When tank 10 has been emptied of its charge of formulation, the process is reversed. That is, tank 20 now serves as the supply tank and tank 10 serves as the receiving tank for a second pass of the material through the milling machine. In this case, the material exits tank 20 through valve 330 and feed line 140 to pass through three-way valve 320 and pump 80 which forces the mixture through the bead mill 40. The material leaving the bead mill 40 passes through the in-line particle size analyzer 60 and three-way valve 340, but now is directed through line 160 into tank 10 which serves as the receiving tank. This process is repeated with multiple passes through the bead mill 40 until the desired reduction in solids particle size has been achieved. This event is signaled by in-line particle size analyzer 60 which sends a signal through signal line 430 to controller 70 which then signals the shut-down of the milling process.

The tank last holding the formulation when the desired particle size has been achieved is then disconnected from the system and wheeled to the location where it serves as the supply tank for the subsequent aerosol canister filling operation.

The following examples are typical of the aerosol formulations which can be prepared by the process of the present invention and are provided to enable one skilled in the art to practice the invention. The examples are to be viewed as merely illustrative of the invention and are not to be read as limiting its scope as it is defined by the appended claims. In each of the examples, the therapeutic agent, surfactant, and propellant/milling medium are mixed in the initial supply tank of the process apparatus under dry nitrogen gas. The mixture is passed through the mill to the receiving tank and back again to the initial tank until the desired particle size, generally below about 10 μm, is achieved. At that point, the tank holding the milled formulation is disconnected from the system and moved to the location where the formulation is filled into aerosol canisters and the cap and valve assembly is attached by conventional means known in the art.

EXAMPLE 1

A solid aerosol pharmaceutical formulation containing leuprolide acetate is prepared by mixing 24–28 parts by weight trichlorofluoromethane, 72–76 parts by weight dichlorodifluoromethane, 0.3–0.6 parts by weight sorbitan trioleate, and 10 mg/ml of leuprolide acetate, milling the resulting mixture to a particle size less than about 10 μm, charging the resulting milled mixture to aerosol pressure canisters, and attaching and sealing the cap and valve stem assembly to the filled canisters.

EXAMPLE 2

A solid aerosol pharmaceutical formulation containing leuprolide acetate is prepared by mixing 24–28 parts by weight trichlorofluoromethane, 72–76 parts by weight dichlorodifluoromethane, 0.3–0.6 parts by weight sorbitan trioleate, and 20 mg/ml of leuprolide acetate, milling the resulting mixture to a particle size less than about 10 μm, charging the resulting milled mixture to aerosol pressure canisters, and attaching and sealing the cap and valve stem assembly to the filled canisters.

EXAMPLE 3

A solid aerosol pharmaceutical formulation containing leuprolide acetate is prepared by mixing 25 parts by weight trichlorofluoromethane, 74 parts by weight dichlorodifluoromethane, 0.3 parts by weight sorbitan trioleate, and 10 mg/ml of leuprolide acetate, milling the resulting mixture to a particle size less than about 10 μm, charging the resulting milled mixture to aerosol pressure canisters, and attaching and sealing the cap and valve stem assembly to the filled canisters.

EXAMPLE 4

A solid aerosol pharmaceutical formulation containing leuprolide acetate is prepared by mixing 25 parts by weight trichlorofluoromethane, 99 parts by weight tetrafluoroethane, 0.1 parts by weight sodium lauryl sulfate, 0.1 parts by weight cholesterol, and 10 mg/ml of zileuton, milling the resulting mixture to a particle size less than about 10 μm, charging the resulting milled mixture to aerosol pressure canisters, and attaching and sealing the cap and valve stem assembly to the filled canisters.

We claim:

1. A process for preparing an aerosol pharmaceutical formulation containing a solid therapeutic agent comprising the steps of a) mixing the solid therapeutic agent with a liquid propellant having a boiling point of less than about 25° C. to form a mixture comprising up to 99.9% weight of said liquid propellant;

b) repeatedly passing the mixture formed in step a) between a first refrigerated supply tank and a second refrigerated receiving tank through a milling machine until the particle size of solids contained in the mixture is reduced to less than about 10μ, said first refrigerated supply tank and said second refrigerated receiving tank being kept at a temperature between about −80° C. and about 10° C.; and c) thereafter charging the mixture of solid therapeutic agent and propellant into aerosol canisters.

2. The process according to claim 1 wherein the propellant is selected from the group consisting of alkanes of less than ten carbon atoms, halogenated alkanes of less than ten carbon atoms, cycloalkanes of less than ten carbon atoms, halogenated cycloalkanes of less than ten carbon atoms, dialkyl ethers in which the alkyl groups are independently selected and less than ten carbon atoms, halogenated dialkyl ethers in which the alkyl groups are independently selected and less than ten carbon atoms, dialkyl thioethers in which the alkyl groups are independently selected and less than ten carbon atoms, and halogenated dithioalkyl ethers in which the alkyl groups are independently selected and less than ten carbon atoms.

3. The process according to claim 1 wherein the material employed as both milling medium and propellant is selected from the group consisting of chlorodifluoromethane chlorotrifluoromethane, dichlorodifluoromethane, trichlorofluoromethane, tetrafluoroethane, 1,2-dichlorotetrafluoroethane, trichlorofluoroethane, chloropentafluoropropane, chloroheptafluoropropane, heptafluoropropane, perfluorocyclopropane, perfluoropropane, perfluoro-n-butane, perfluoroisobutane, perfluorocyclobutane, perfluorodimethyl ether, perfluorodiethyl ether, perfluorofuran, perfluoromethylamine, bis-(trifluoromethyl)sulfide, and trifluoromethylpentafluorosulfide.

4. The process according to claim 3 wherein said material employed as both milling medium and propellant is tetrafluoroethane.

5. The process according to claim 3 wherein said material employed as both milling medium and propellant is heptafluoropropane.

6. The process of claim 1 wherein said 10μ particle size is determined by continuous monitoring of the process stream.

* * * * *